United States Patent [19]

Adamovsky

[11] Patent Number: 5,715,047
[45] Date of Patent: Feb. 3, 1998

[54] SCANNING MODE SENSOR FOR DETECTION OF FLOW INHOMOGENEITIES

[75] Inventor: Grigory Adamovsky, Solon, Ohio

[73] Assignee: The United States of America as represented by the Administrator of the National Aeronautics and Space Administration, Washington, D.C.

[21] Appl. No.: 687,062

[22] Filed: Jul. 8, 1996

[51] Int. Cl.$^6$ ................................................. G01N 21/41
[52] U.S. Cl. ............................................. 356/128; 356/129
[58] Field of Search ..................................... 356/128, 129; 73/147, 118.2

[56] References Cited

U.S. PATENT DOCUMENTS

| 3,623,361 | 11/1971 | Funk | 356/129 |
|---|---|---|---|
| 3,693,015 | 9/1972 | Funk | 356/129 |
| 4,493,217 | 1/1985 | Engler et al. | 73/861.27 |
| 4,547,071 | 10/1985 | Teitelbaum | 356/129 |
| 4,652,120 | 3/1987 | Sell | 356/129 |
| 4,784,494 | 11/1988 | Pawliszyn | 356/128 |
| 4,879,895 | 11/1989 | Sajben | |
| 5,072,612 | 12/1991 | Iverson et al. | 356/129 |
| 5,118,931 | 6/1992 | Udd et al. | |
| 5,283,430 | 2/1994 | Carlin et al. | |
| 5,387,792 | 2/1995 | Carlin et al. | |
| 5,424,824 | 6/1995 | Daiber et al. | |

OTHER PUBLICATIONS

Proceedings of The International Society for Optical Engineering . . . San Diego, CA "Optical techniques for shock visualization and detection" G. Adamovsky . . . Jul. 10–13, 1995.

*Primary Examiner*—Richard A. Rosenberger
*Attorney, Agent, or Firm*—Kent N. Stone; Susan D. Reinecke

[57] ABSTRACT

A scanning mode sensor and method is provided for detection of flow inhomogeneities such as shock. The field of use of this invention is ground test control and engine control during supersonic flight.

Prior art measuring techniques include interferometry, Schlieren, and shadowgraph techniques. These techniques, however, have problems with light dissipation.

The present method and sensor utilizes a pencil beam of energy which is passed through a transparent aperture in a flow inlet in a time-sequential manner so as to alter the energy beam. The altered beam or its effects are processed and can be studied to reveal information about flow through the inlet which can in turn be used for engine control.

3 Claims, 6 Drawing Sheets

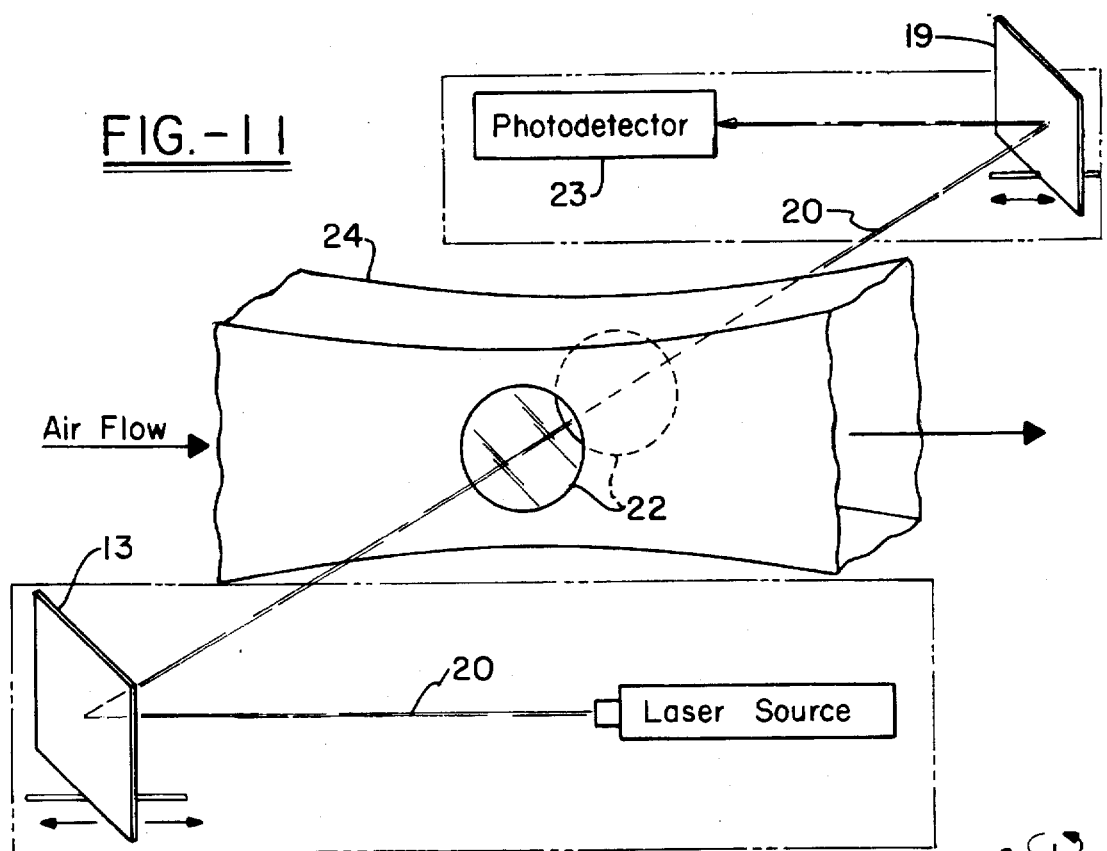
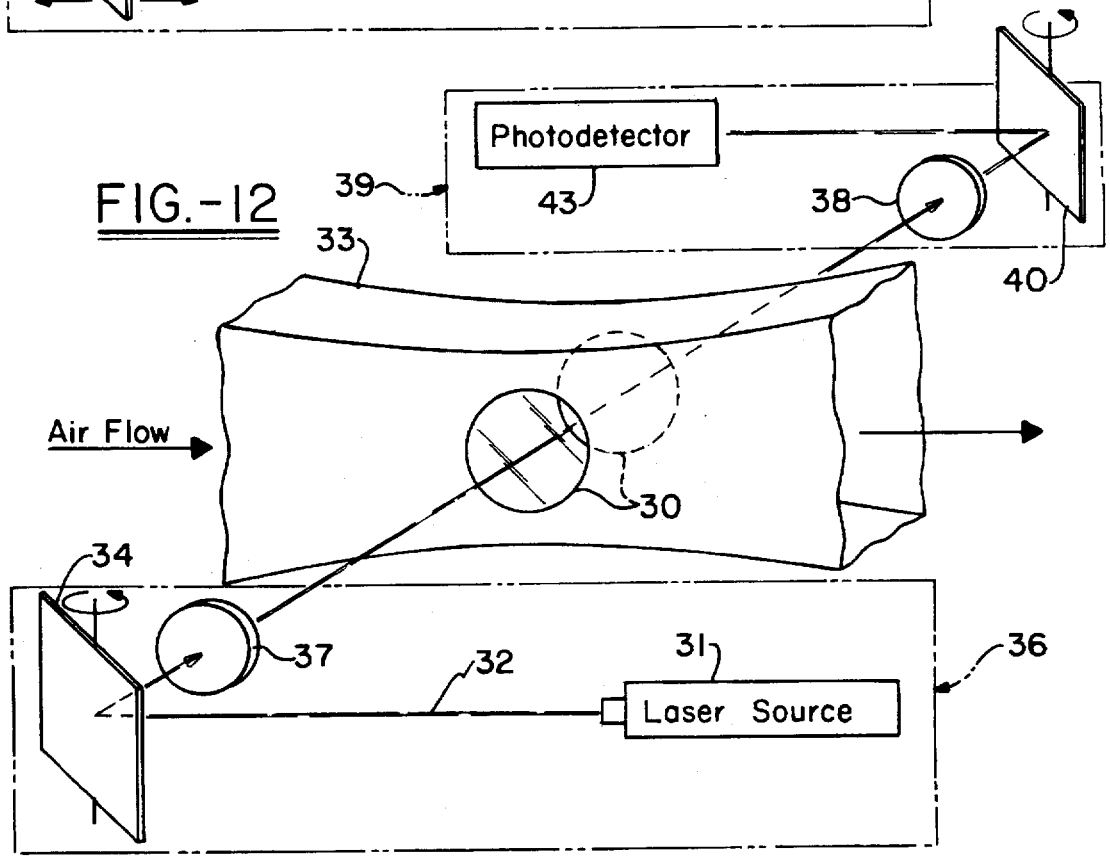

SCANNING MODE SENSOR FOR DETECTION OF FLOW INHOMOGENEITIES

ORIGIN OF THE INVENTION

The invention described herein was made by an employee of the United States Government and may be manufactured and used by or for the Government for Government purposes without the payment of any royalties thereon or therefor.

TECHNICAL FIELD

The invention relates to a method and apparatus for sensing flow inhomogeneities such as for example normal shock involved in ground test facilities and in engine control during supersonic flight. More specifically, the invention relates to the use of a scanning mode flow position sensor having potentially higher optical power density throughput, and as can be used to determine shock and other flow conditions associated with shock.

BACKGROUND OF THE INVENTION

Visualization of flow inhomogeneities have widespread application. One example of such application includes the location of a shock as eventually applied in engine control during flight and flight testing. The need for shock position sensors capable of meeting flight qualifying requirements has been recognized and attempts have been made to develop such sensors. Early efforts were concentrated around using pressure taps along the inlet walls. The positions of the shock were determined by tracking the pressure readings and locating the pressure jump associated with the shock. This basic technique evolved in several wall pressure-based configurations of normal shock position sensing systems.

Despite apparent initial success, these wall pressure-based measuring techniques have serious drawbacks. The most important are slow response due to pneumatic manifolds used and the negative effect of boundary layers on the stability of pressure readings. These problems seriously restrict applicability of those techniques to normal shock detection and control during supersonic flight. For a commercial aircraft, economic efficiency has to be achieved. As a result, the control system is required, in addition to avoiding an un-start, to provide the most economical operating regime for the engine (achieved by minimizing fuel consumption). Such shock requirement can be met by accurate measurements of the normal shock position. However, prior art shock position sensing techniques may not optimize efficient engine control.

Simple prior art measuring techniques that do not have the problem of the wall pressure-based measuring techniques involve optical visualization and are widely used in ground-based flow analyzing facilities. The fundamental feature of these techniques is that the flow can be observed and analyzed directly and almost instantaneously. Three basic known flow visualization techniques are interferometry, Schlieren, and shadowgraph.

Patterns generated by an interferometer visualize density distributions and those generated by Schlieren are used to detect first derivatives of the density distribution. Patterns observed in the shadowgraph system are generated by second order derivatives of the density distribution. Thus, shocks which are being created by very rapid changes in densities are observed best by the shadowgraph. At the same time, minor and slowly varying changes in density that can be well observed by an interferometer and Schlieren represent noise and are omitted by the shadowgraph. These properties of the shadow-graph, along with good mechanical stability and a small number of required components, make the shadowgraph-based system a major candidate for consideration as an airborne shock position sensor.

U.S. Pat. No. 5,283,430 relates to a method of normal shock sensing where a modulated signal is coupled to a single fiber as a sum total of all the wavelength components. The position of shock is identified in a spectrum by a shadow or absence of a signal at a certain optical frequency.

U.S. Pat. No. 5,387,792 is a related application for measuring the position of a shadow-producing object.

There are problems with the prior art, however, such as the power budget, i.e., light dissipation which results in difficulty in detection. In a sensing system with color coding, light from a broad band source is delivered to a test section by a single fiber. The light is then spread and collimated to fill an area in a section of the supersonic inlet where shock is expected to appear. This inlet section can be considered a "test section." A variable spectral filter on the other side of the test section transforms the broad band spectrum of the light into a space spectrally modulated signal. The light which carries this modulated signal is collected and sent to the detector via a single fiber. The light passing through the system experiences great loss. To compensate for this loss, the electronics have to have high gain and this results in a relatively low bandwidth and a slower system response.

Additional prior art considerations include the flow conditions in the inlet such as change or displacement in back pressure. The measurement of such conditions may be influenced by the sensor placement within the inlet. The present invention could allow broader variety in sensor placement as a result of higher optical density throughput.

DISCLOSURE OF INVENTION

The present invention relates to the use of scanning mode flow visualization systems for determining flow inhomogeneities such as shock position. The invention can be used with various types of shock such as normal shock, diamond shock, bow shock and the like. These systems involve the use of a sensing element which causes a narrow beam, i.e., a pencil beam, of light to penetrate the flow in the direction normal to flow and scan the flow (through a transparent opening or aperture in the test section) in a time-sequential manner. As used herein, "transparent opening" refers to an opening area or condition which permits the passage of a test beam at a given wavelength. It is therefore possible that the opening would block or otherwise hinder the passage of irrelevant wavelength. The narrow beam used is concentrated with respect to the test area and the wavelength of the light beam. For example, for a beam of light generally having a wavelength in the order of a micron for a test area of 12 to 15 inches, the beam diameter may be from 0.2 to 2.5 millimeters depending somewhat on the distance of the source from the test area. This is in contrast to conventional prior art systems in which light fills the entire aperture simultaneously, causing the spatial power density of the light to drop. Consequently, the present invention utilizes various embodiments to achieve the desired results, such as electro-mechanical scanners, acousto-optical scanners, and spectral scanners.

It is therefore an object of the present invention to provide a flow visualization sensor having a higher optical power density throughput.

An additional object of the present invention is to provide a time-dependent intensity distribution across the photodetector which could correspond to an intensity distribution obtained by conventional prior art shadowgraph techniques.

The above-noted objects are met by the use of a scanning mode shock position sensor. In accordance with the invention a scanning element is used to scan by passing a narrow beam of light through an aperture located in a test section of a supersonic inlet in a time-sequential manner. A receiver senses the intensity and/or wavelength of the light on the opposite side. The beam is directed generally perpendicularly of the flow direction. The data is collected to provide a time-dependent intensity distribution.

Various means can be used to generate and direct the light beam.

BRIEF DESCRIPTION OF DRAWINGS

FIG. 11 is a second view representing the scanner of FIG. 2; and

FIG. 12 is a second view representing the scanner of FIG. 3.

DETAILED DESCRIPTION OF THE INVENTION

Figure 1:
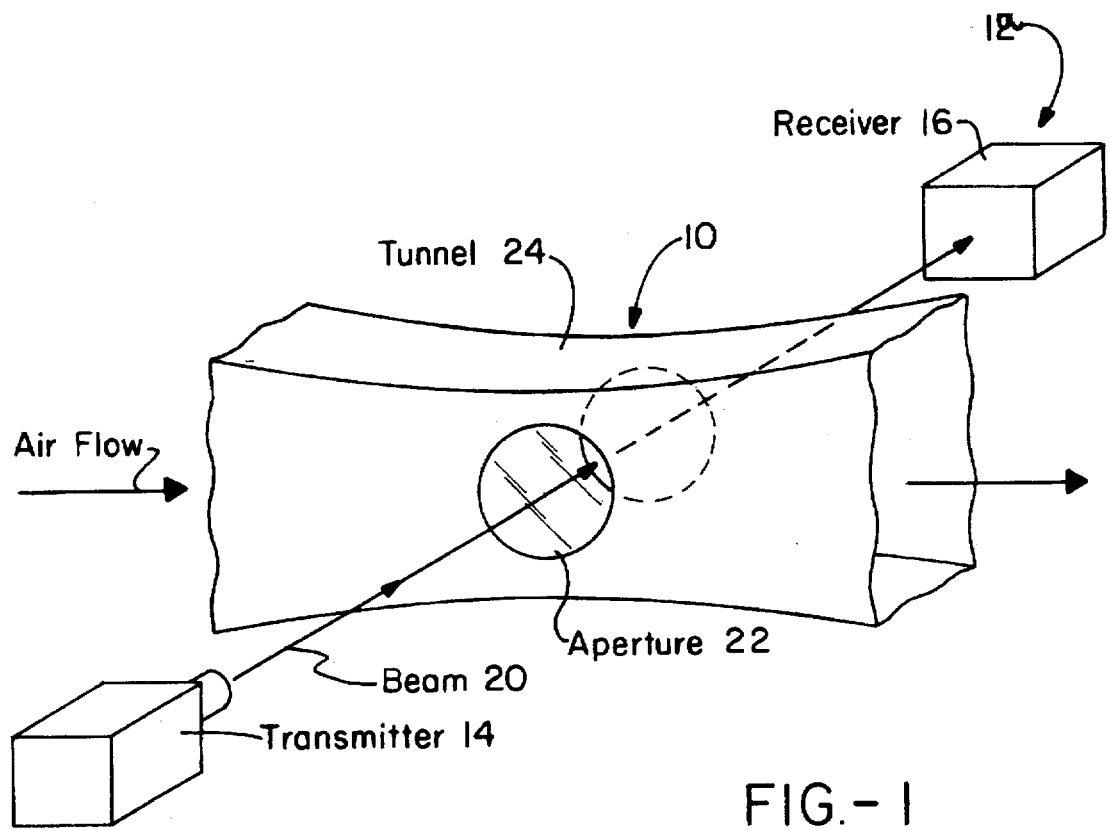
FIG. 1 is a representation of the scanning apparatus in accordance with the invention.

The above-noted objects are met by the use of a scanning mode flow visualization system shown generally at 10 in FIG. 1. In accordance with the invention, a scanning element 12 comprising a transmitter 14 and a receiver 16 is used to scan by passing a narrow beam or pencil beam 20 of light through an aperture 22 located in a test section of a flow inlet (i.e., a tunnel 24) in a time-sequential manner. Time-sequential manner is used herein to indicate that the scanning varies with time, i.e. different locations of the test section are scanned at different times and not all at once. The receiver or signal processor 16 senses and processes the intensity and/or wave length of the light on the opposite side of the flow wave. The beam 20 is directed generally perpendicular to the flow direction. The data is collected to provide a time dependent intensity distribution.

In accordance with the different embodiments of the invention, various means can be used to generate and direct the light beam. For example, the system can utilize electromechanical, acousto-optical, and spectral scanning mechanisms.

The use of a scanning system contributes flexibility to the flow visualization techniques by contributing information with respect to flow conditions associated with shock such as Mach number and static. The utilization of the laser beam scattering properties of the shocks may require a receiving unit with either a detector or fiber array which would display a spatial intensity distribution of the scattered light. System capability may be enhanced by using a combination of the beam-spreading and color-encoding techniques.

A "pencil beam" is a narrow beam of light or other electromagnetic radiation which has a low divergence. The low divergence keeps the diameter of the beam approximately the same over relatively large distances. Sometimes the pencil beam is also presented as a bundle of individual rays propagating in the same direction. As used herein a "pencil beam" may comprise a number of individual light bundles propagating in the same direction. These individual pencil beams may have either the same or different wavelengths and/or may be modulated at different wavelengths.

There is a relationship between the wavelength of radiation, the beam diameter, and the beam divergence. In the present case, the source of radiation is a HeNe laser with a wavelength of 632.8 nm. The laser emits a beam of light with a diameter of approximately 0.5 mm that propagates with a very low divergence, practically without changing its diameter over relatively large distances.

The basic rationale as to how the pencil beam has been selected is as follows:

a) The wavelength has to be in the visible region of the electromagnetic spectrum;

b) The beam diameter has to be much smaller than the transparent aperture in the test section and comparable in size with the disturbance to be observed (sometimes even smaller);

c) The beam has to maintain approximately the same diameter while propagating in homogeneous media over a distance equal to the distance from the source to the detector.

It is obvious that the laser selected meets those criteria. However, in general, the selection of the wavelength in the visible region of the spectrum is not a requirement, rather a convenience (it is visible). UV, infrared, microwave, and even RF sources could also be used as long as a pencil beam can be generated.

Figure 2:
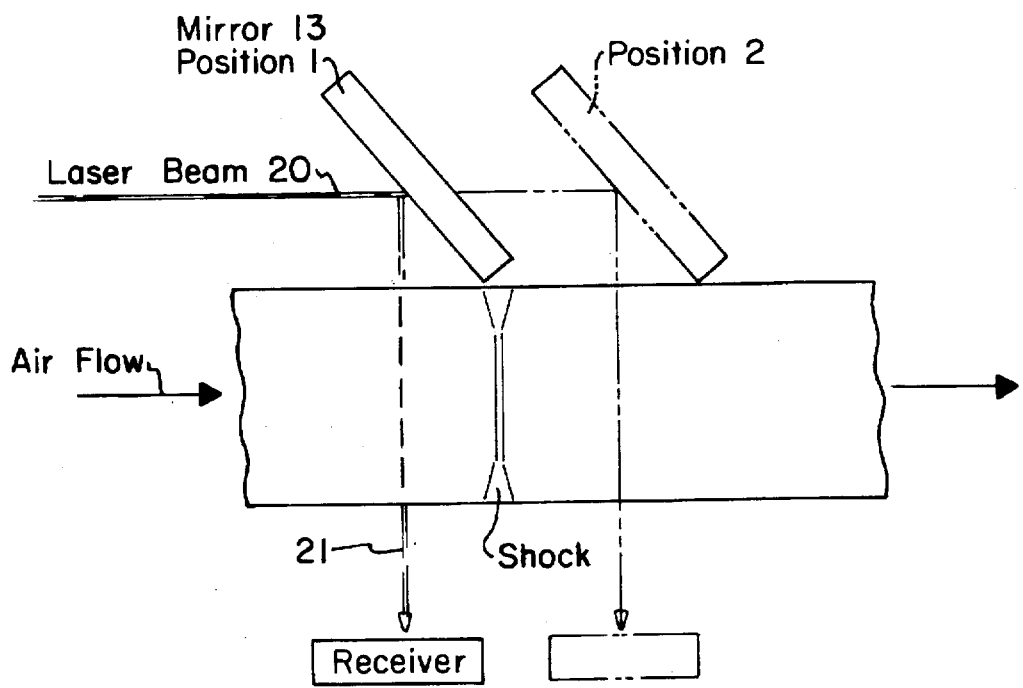
FIG. 2 is a schematic representation of a linear scanner in accordance with the invention.

In a first embodiment as shown in FIGS. 2 and 11, an electromechanical scanner 30 is used. Electromechanical scanners comprise optical mirrors or prisms that reflect light in a certain direction according to the law of reflection. By changing a position of the reflecting surface with respect to the incident beam the direction of the reflected beam also will be changed. Two basic types of electromechanical scanners, linear and angular, can be used. In a sensing system with a linear scanner as shown in FIGS. 2 and 11, a reflecting mirror 13 or prism moves linearly by means of a translation stage or the like, in a direction parallel to the flow direction of a shock wave and reflects the incident beam under a certain angle 21. A light source such as a laser provides the light. Thus, the beam of light is scanned through a plane in the test section 24 by providing an aperture 22 where the normal shock is expected. After passing through the aperture 22 the scanning pencil beam enters the receiving unit 16 of the system. In the simplest case, the receiving unit 16 may consist of a "CCD" (charge-coupled device), a type of detector that gives intensity as it relates to position. This is an example of a type of suitable position-sensitive device, a photodetector array, or a similar position sensitive detector. As is shown in FIG. 11 after passing through the aperture 22, the beam 20 is reflected from a reflector 19 on a translation stage which is coordinated to the movements of the first translation stage to a photodetector 23. A coherent fiber bundle may also be used in the receiving unit to capture the pencil beam. The fiber bundle then delivers the light to a remotely located position sensitive detector. Alternatively as shown in FIG. 6, the beam 20 can be focused using a focusing lens 15 and reflected through a rotating reflector 17 in order to align the beam with a photodetector 18.

Figures 5, 6:
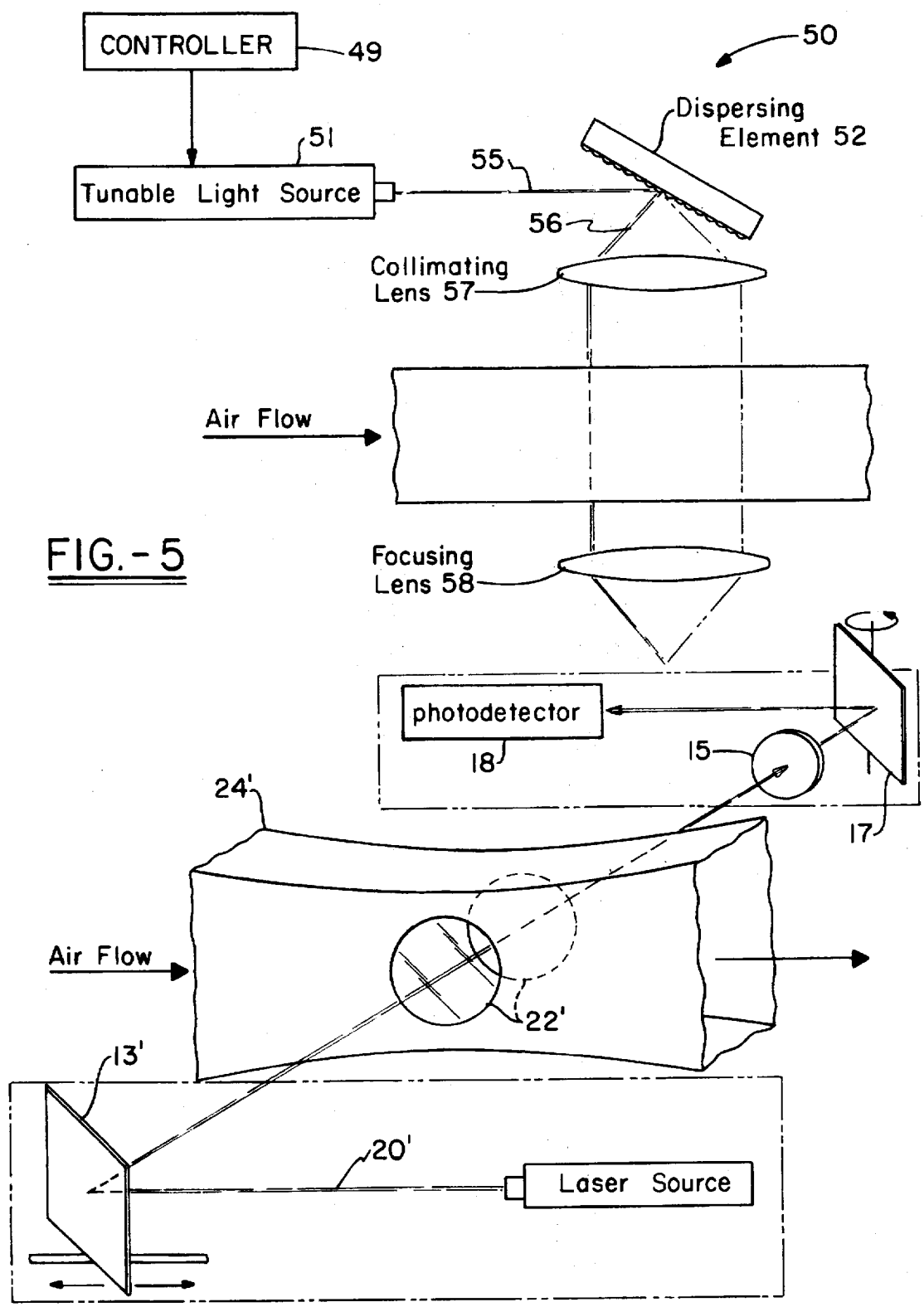
FIG. 5 is a schematic representation of a spectral scanner in accordance with the invention.
FIG. 6 is a representation of a hybrid electro-mechanical scanner in accordance with the invention.

Another embodiment of the receiving unit 16 as illustrated in FIG. 6 involves a lens 61 with a single fiber 63 or fiber bundle in its focal plane. This configuration permits detection of transmission properties of the flow.

In a further example of a simple linear scanning system, the transmitting part of the system is comprised of a HeNe laser and a beam-splitting cube which is mounted on a translation stage. The laser beam reflects from the reflecting surface of the cube and passes through a transparent portion of a convergent-divergent nozzle. The direction of the laser beam after reflection is normal to the direction of the flow. The receiving unit of the system consists of a "CCD" array.

Figure 3:
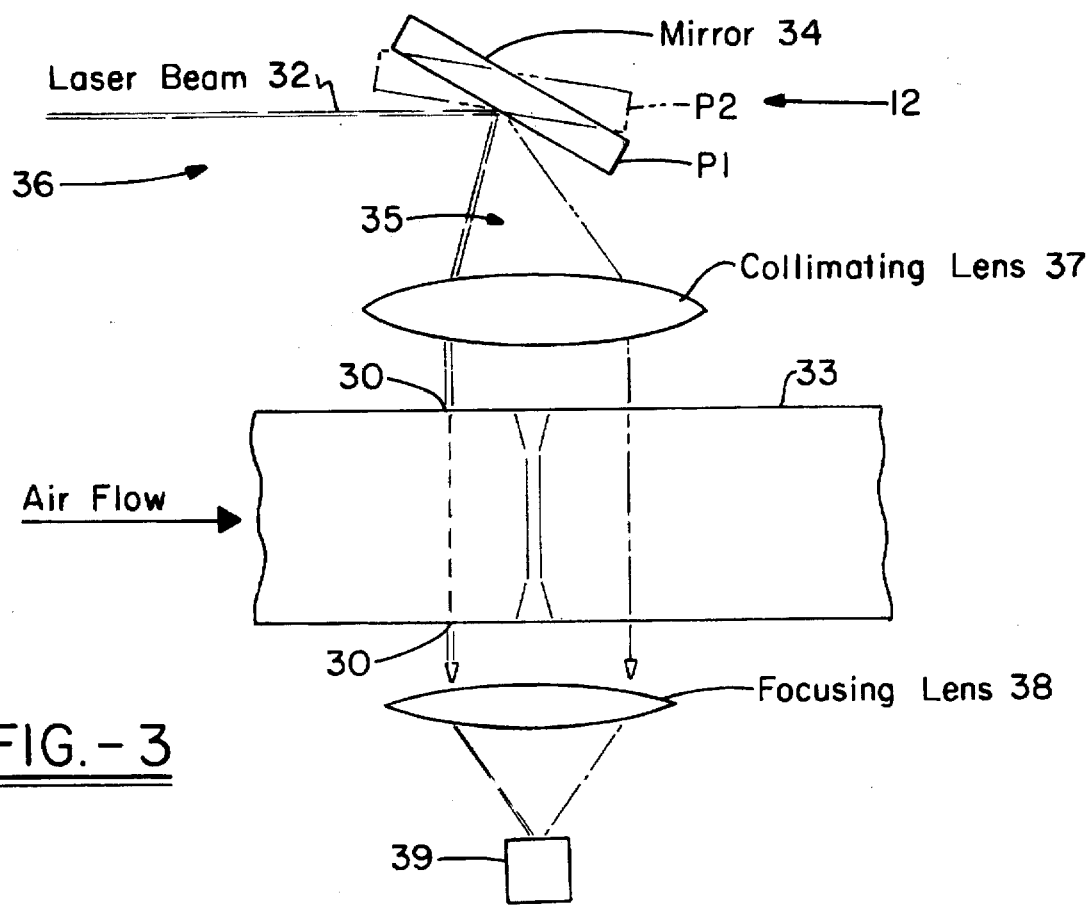
FIG. 3 is a schematic representation of an angular scanner in accordance with the invention.

A different embodiment shown in FIGS. 3 and 12 utilizes a sensing system 12 with an angular scanner. In this embodiment, a reflecting mirror 34 or prism rotates around a certain axis in a prescribed manner to reflect the laser beam 32 so as to produce a sector of light 35. The axis is at the reflecting surface of the scanner from which the incident beam reflects. A transmitter 36 comprising the light source 31 and mirror 34 is used to scan through an aperture or apertures 30 in the test section 33. The sector of light reflected from the mirror 34 passes through a collimating lens 37 and through a focusing lens 38. The transmitter 36 and the collimating lens 37 are positioned in such a way that the focal point of the lens 37 lies on the rotational axis of the mirror 34 as well as on the axis of a second rotating mirror 40. A photodetector 43 receives the light. The system may have linear or angular scanners on both the transmitting and receiving sides of the test section. It may also be a hybrid electromechanical system with a linear scanner on one side of the test section and an angular scanner on the other side such as illustrated in FIG. 6. In this embodiment the beam 20' is reflected in a reflector 13' on a translation stage through apertures 22' in a tunnel which defines a test section 24'. The beam 20' is focussed in a focussing lens 15 and reflected in a rotating reflector 17 and finally registered in a photodetector 18. The signal processing algorithm is similar for both linear and angular electromechanical scanners. If appropriate temporal synchronization techniques are used, a time-dependent intensity distribution across the photodetector corresponds to an intensity distribution for flow conditions obtained by a conventional shadowgraph technique under the same conditions.

Figure 4:
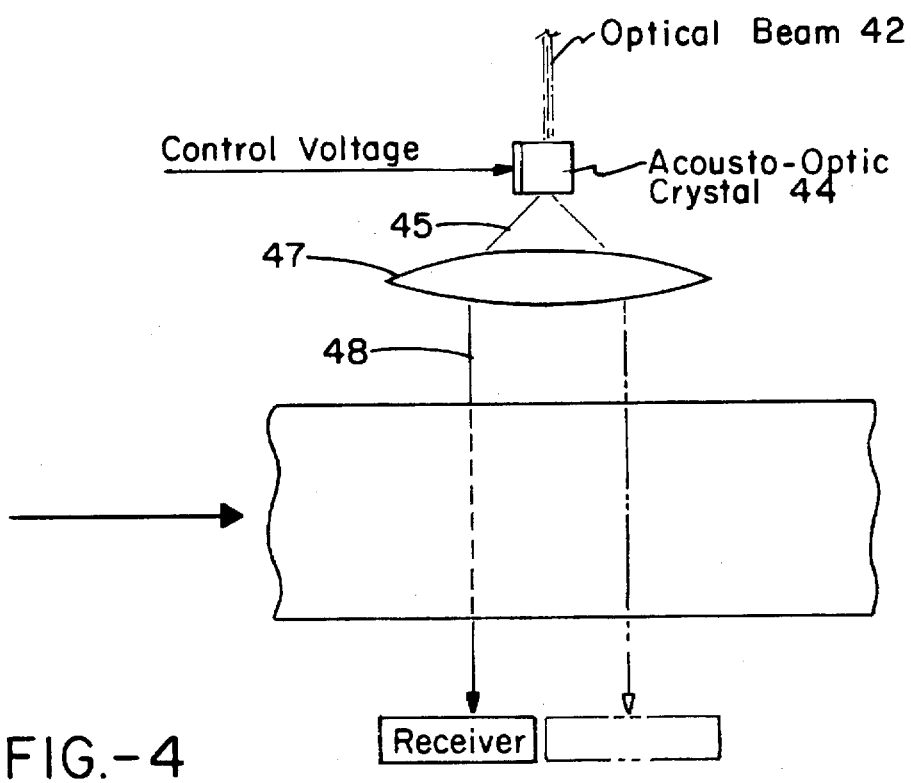
FIG. 4 is a schematic representation of an acousto-optical scanner in accordance with the invention.

Yet another embodiment shown in FIG. 4 of the invention relates to acousto-optical scanners. The principle of acousto-optical scanners is similar to electromechanical ones and utilizes a laser beam 42. The major difference is that an electromechanically driven reflecting surface is replaced by an acousto-optical deflector 44 which acts on the beam 42 to create a sector 45. The deflector 44 is placed in the focal point of the collimating lens 47 in such a way that the beam 42 that exits the lens 47 is always normal to the flow direction. The rest of the system remains practically the same.

A further embodiment shown in FIG. 5 utilizes a spectral scanner. Major components in spectral scanners are a tunable light source 51 and an optical dispersive element 52. Examples of the dispersive elements are dispersion prisms and diffraction gratings. These components are installed in the transmitting part 50 of the sensing system, which also includes a controller 49. The tunable source 51 generates a narrow beam of light 55 (i.e., a pencil beam) whose optical frequency changes in time in a prescribed manner. It is a known fact that the direction of a light beam after interaction with a fixed dispersive element 52 depends on the optical frequency of the light. This space-frequency or space-wavelength scanning generates a "rainbow" 56 with the difference that each "color" appears in its place at a given time. The pencil beam may contain several individual beams with different optical frequencies (wavelengths). The wavelengths may be cooperatively or independently changed in a time-prescribed manner. Thus, the fixed dispersive element produces several "rainbows." The term "fixed" is used to indicate spectral scanning by a stationary dispersive element in contrast with other embodiments in which the light beam is physically translated or otherwise manipulated.

The optical dispersive element may also replace a reflecting mirror or prism in the angular scanner. Such a hybrid system combines a spectral scanner with an angular electromechanical one. The hybrid scanner may also employ a plurality of optical beams with different wavelengths. These optical beams strike the angular scanner which has its reflecting element, mirror or prism, replaced by the dispersive element. A multiplicity of spectral cones or "rainbows" will result.

The dispersive element is positioned at the focal point of a collimating lens 57. In the receiving part of the system, the "rainbow" is collected by a focusing lens 58 similar to the one used in electromechanical scanners.

EXAMPLE

Figure 7:
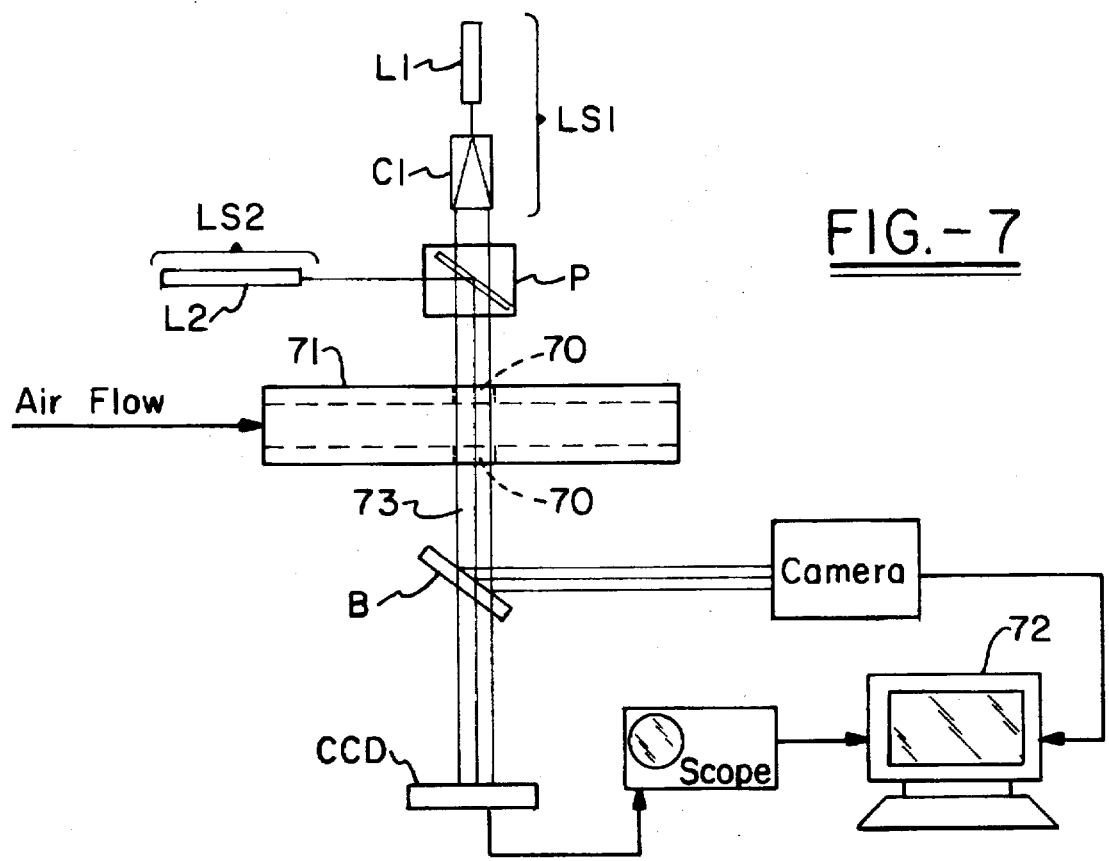
FIG. 7 is a schematic representation of the principle configuration of the experiment in accordance with the Examples.

An experiment was conducted using a test apparatus as shown in FIG. 7. The test apparatus consisted of a test section having a transparent window 70 of plexiglass transverse to a hollow section otherwise made of aluminum. The test section was connected to a small-necked (i.e., minimum throat of 17.9×17.9 mm$^2$), convergent-divergent ("CD") nozzle in a flow-tight connection with a shop air supply. The "CD" nozzle had an area to yield a maximum Mach number of 1.8. Two laser systems, LS1 and LS2, were used, the first of which utilized a 3 mW HeNe laser L1 and collimating device to create a wide collimated beam with relatively uniformly distributed intensity. This was used as a traditional shadowgraph. The second laser system, LS2, was a single 0.5 mW HeNe laser which emits a narrow pencil beam. The two beams were superimposed and aligned in the same direction by means of a beam-splitting prism. The combined beam passed through the test section 71 and through the beam splitter B to the photo camera and "CCD" array. An oscilloscope was used to observe the intensity distribution and a computer connected to the camera and oscilloscope was used for data acquisition and analysis.

Using this test apparatus, shock was studied using the collimated beam produced by the laser system LS1 and the resultant shadow was observed, while the pencil beam from laser system LS2 was used to penetrate the flow in the vicinity of the shock in a direction perpendicular to flow. The test section was scanned by the pencil beam in a time-sequential manner by scanning across the test section transverse to the flow direction. The beam-splitting prism P was mounted on an electronically controlled translation stage. As the pencil beam passed through the regions in the flow with strong changes in density, the circular cross-sectional shape of the beam became deformed.

Figure 8:
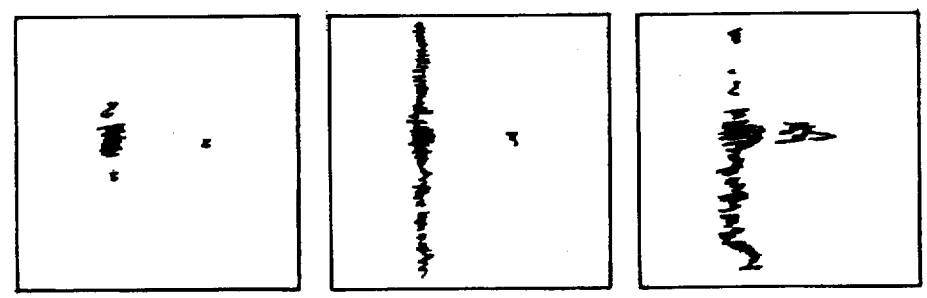
FIGS. 8A, B, and C are representations of photographs of a laser beam after passing through the windows of the nozzle in which FIG. 8A has no flow, FIG. 8B has flow without shock.
FIG. 8C shows a beam intersecting a shock.
Figure 9:
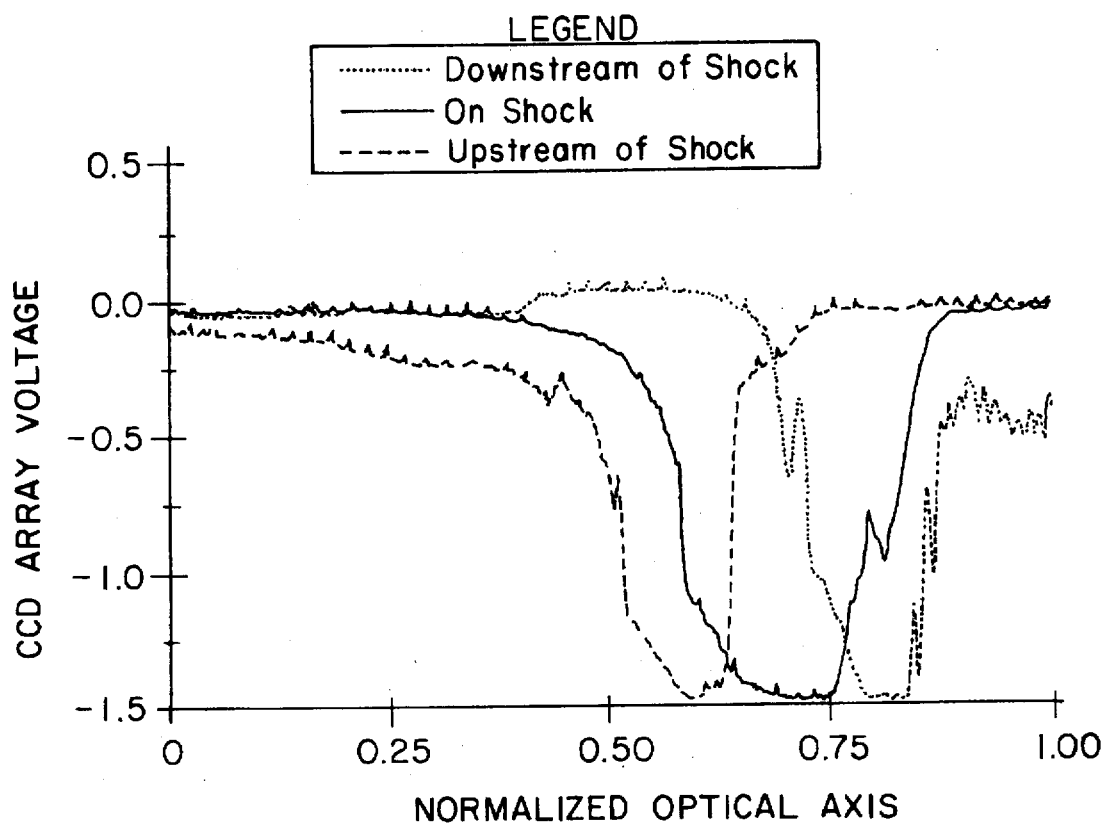
FIG. 9 illustrates the intensity distribution of the pencil beam in smaller nozzle at three locations under flow conditions which yield a shock of the example.
Figure 10:
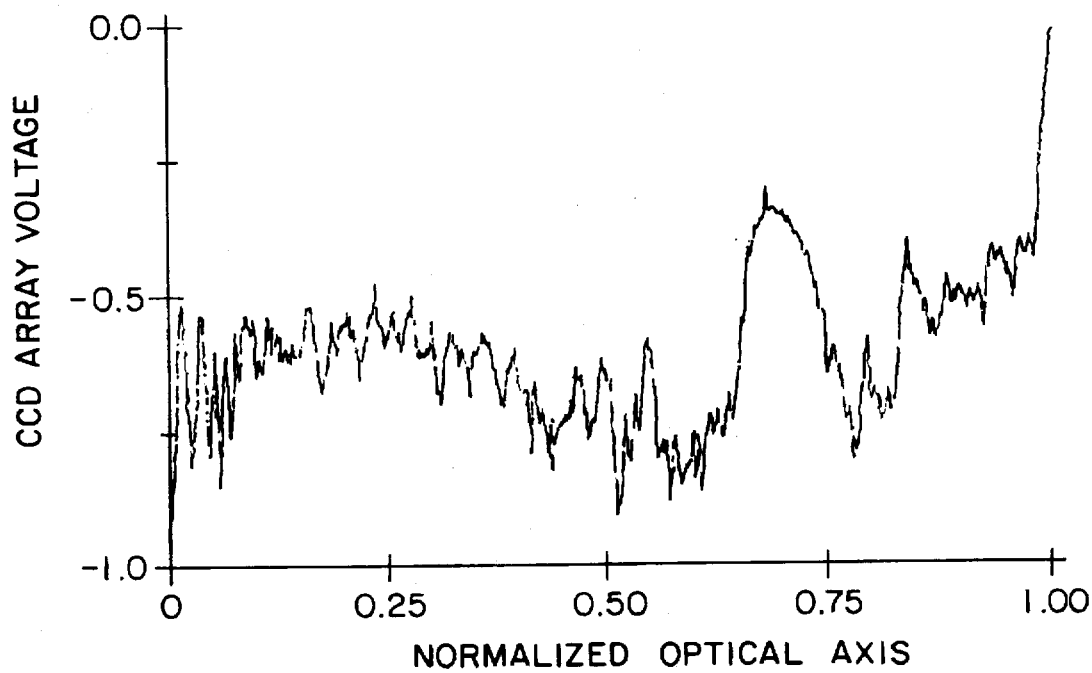
FIG. 10 is a shadowgraph of the flow in the test cell under the same conditions as in FIG. 9.

The results of the experiment obtained by the photo camera and "CCD" array are shown in FIGS. 8, 9, and 10. FIG. 8 shows photographs of the laser beam after passing through the test section in which there is no flow in 8A; there is flow without shock in 8B; and there is a beam intersecting shock in 8C. It can be seen from these pictures that the interaction of a pencil beam with a shock produces a smearing of the beam. The smearing and tail associated with it occur in the direction of flow. The phenomenon is explained by the fact that the air density of a subsonic flow downstream of the shock is higher than the air density of a supersonic flow upstream of it. The air density gradient causes the beam to refract in the direction of flow. Thus, the beam smearing and tail result.

Using the "CCD" array placed 1 meter away from the test cell, FIG. 9 shows the intensity distribution of the pencil beam at three different locations in the nozzle under flow conditions which yield a shock. From FIG. 10 (the shadowgraph of the test cell under the same conditions generated using LS1), the existence of a shock from the bump on the graph can be identified. The intensity profile of the pencil beam is represented in FIG. 10 as a pulse-like signal of almost constant amplitude due to saturation of the "CCD" array. A significant increase in the width of the pulse is observed when the beam is passing through the shock. This increase is also a manifestation of the beam smearing and tail.

While in accordance with the patent statutes the best mode and preferred embodiment has been set forth, the scope of the invention is not limited thereto, but rather by the scope of the attached claims.

What is claimed is:

1. A method of visualization of flow to study shock in a test section inlet where the flow is expected, comprising the steps of:
    providing an aperture in said test section which is transparent in a direction substantially perpendicular to the expected flow direction;
    providing a plurality of laser-generated pencil beams of light, and modifying said beams with scanner means which modifies the optical frequencies of said beams in a time-prescribed manner;
    passing said modified beams through the aperture;
    receiving and processing said beams in a location spaced apart from said aperture.

2. A method as set forth in claim 1 wherein said scanner means comprises an angular scanner which modifies said plurality of light beams subsequently passed through said aperture.

3. An apparatus for the visualization of containing a shock in a test section inlet comprising:
    a transparent aperture in said test section inlet in the vicinity of the shock;
    a plurality of tunable lasers with different ranges of optical frequencies which provide sources of pencil beams of light to pass said beams through said transparent aperture;
    means to tune said plurality of lasers to modify said pencil beams in a time-sequential manner prior to passing said beam through said aperture; and
    means for receiving the beams which passed through said aperture.

\* \* \* \* \*